United States Patent
Cho et al.

(10) Patent No.: US 7,135,572 B2
(45) Date of Patent: Nov. 14, 2006

(54) DIARYL 1,2,4-TRIAZOLE DERIVATIVES AS A HIGHLY SELECTIVE CYCLOOXYGENASE-2 INHIBITOR

(75) Inventors: Il-hwan Cho, Seoul (KR); Jee-woong Lim, Gyeonggi-do (KR); Ji-young Noh, Busan (KR); Jong-hoon Kim, Gyeonggi-do (KR); Sang-wook Park, Gyeonggi-do (KR); Hyung-chul Ryu, Gyeonggi-do (KR); Je-hak Kim, Gyeonggi-do (KR); Jong-ho Kim, Gyeonggi-do (KR); So-young Wang, Seoul (KR); Dal-hyun Kim, Gyeonggi-do (KR); Chun-seon Lyu, Gyeonggi-do (KR)

(73) Assignee: CJ Corp (KR)

( * ) Notice: Subject to any disclaimer, the term of this patent is extended or adjusted under 35 U.S.C. 154(b) by 0 days.

(21) Appl. No.: 11/224,787

(22) Filed: Sep. 12, 2005

(65) Prior Publication Data
US 2006/0009495 A1   Jan. 12, 2006

Related U.S. Application Data

(62) Division of application No. 10/498,157, filed as application No. PCT/KR02/02447 on Dec. 27, 2002.

(30) Foreign Application Priority Data
Dec. 28, 2001   (KR) ........................... 2001-0086698

(51) Int. Cl.
*C07D 401/04*   (2006.01)
(52) U.S. Cl. ................................... 546/272.4
(58) Field of Classification Search ............. 546/272.4
See application file for complete search history.

(56) References Cited

U.S. PATENT DOCUMENTS 6,239,137 B1   5/2001   Karmali et al.
6,753,332 B1 *   6/2004   Sakya et al. ................ 514/273
2003/0125368 A1   7/2003   Sakya et al.
2005/0075507 A1   4/2005   Cho et al.

FOREIGN PATENT DOCUMENTS

EP   1 099 695   5/2001
WO   WO 99/12930   3/1999

* cited by examiner

Primary Examiner—Patricia L. Morris
(74) Attorney, Agent, or Firm—Swanson & Bratschun, LLC

(57) ABSTRACT

The present invention relates to a novel diaryl 1,2,4-triazole derivative of the following formula 1 as a highly selective cyclooxygenase-2 inhibitor:

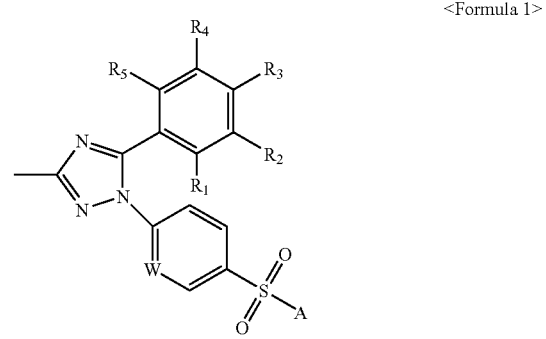

<Formula 1>

Wherein, $R_1$, $R_2$, $R_3$, $R_4$, $R_5$, W and A is as defined in this specification.

1 Claim, No Drawings

DIARYL 1,2,4-TRIAZOLE DERIVATIVES AS A HIGHLY SELECTIVE CYCLOOXYGENASE-2 INHIBITOR

This application is a divisional application of U.S. application Ser. No. 10/498,157, filed Jun. 8, 2004, entitled "Diaryl 1,2,4-Triazole Derivatives as a Highly Selective Cyclooxygenase-2 Inhibitor," which application 1s a 35 U.S.C. § 371 national phase application of PCT/KR2002/002447 (WO 03/055875), filed on Dec. 27, 2002, entitled "Diaryl 1,2,4-Triazole Derivatives as a Highly Selective Cyclooxygenase-2 Inhibitor," which claims priority to Korean Application No. 2001-0086698, filed Dec. 28, 2001. Each of these applications is incorporated herein by reference in its entirety.

TECHNICAL FIELD

The present invention relates to diaryl 1,2,4-triazole derivatives as a highly selective cyclooxygenase-2 inhibitor.

BACKGROUND

Most of non-steroid anti-inflammatory drugs represent actions such as anti-inflammation, analgesic, and antipyretic activity by inhibiting the enzymatic activity of cyclooxygenase or prostaglandin G/H synthase. In addition, they can suppress the uterine contraction induced by hormones and the cell proliferation in several kinds of cancers. First, only cyclooxygenase-1 was known to be found in cow as a constitutional enzyme. But recently, cyclooxygenase-2 is identified to be discriminated clearly from cyclooxygenase-1 and can be provoked easily by mitogen, endotoxin, hormones, growth factors, cytokines and the like.

Prostagladins have various pathological and physiological functions. Precisely, cyclooxygenase-1 as a constitutional enzyme participates in the secretion of basic endogenous prostaglandin and plays an important role in physiological aspects such as stomach homeostasis, renal blood circulation and so on. On the other hand, cyclooxygenase-2 is induced by inflammatory factors, hormones, growth factors, cytokines and the like, and thus plays an important role in pathological effects of prostaglandins. Therefore, selective inhibitors against cyclooxygenase-2 are expected to have no side effect on account of the functional mechanism compared with the anti-inflammatory drugs such as conventional non-steroid agents and to represent actions such as anti-inflammation, analgesic, and antipyretic activity. Furthermore, it is estimated to suppress the uterine contraction induced by hormones and the cell proliferation in several kinds of cancers. Especially, it probably has a few side effects such as gastrointestinal toxicity, renal toxicity and the like. Also, it is assumed to prevent the synthesis of contractive prostanoids, and thus inhibit the contraction of smooth muscle induced by the prostanoid. Hence, it can be applied usefully to treat a premature birth, dysmenorrhea, asthma and several diseases associated with eosinophilic leukocytes. Besides, it can be widely exploited to cure osteoporosis, glaucoma and athymia, which has been disclosed in many references, especially the usefulness of selective inhibitors against cyclooxygenase-2 (References: John Vane, "Towards a better aspirin" in Nature, Vol. 367, p 215–216, 1994; Bruno Battistini, Regina Botting and Y. S. Bakhle, "COX-1 and COX-2: Toward the Development of More Selective NSAIDs" in Drug News and Perspectives, Vol. 7, p 501–512, 1994; David B. Reitz and Karen Seibert, "Selective Cyclooxygenase Inhibitors" in Annual Reports in Medicinal Chemistry, James A. Bristol, Editor, Vol. 30, p 179–188, 1995).

The selective inhibitors against cyclooxygenase-2 have been reported to have various structure forms. Among these, the diaryl heterocycle structure, namely a tricyclic system, has been studied most frequently and exploited to construct a lot of candidate substances. In this structure, it is essential that sulfonamide or methanesulfone group exist onto one phenyl group. The initial substance having the above structure is identified to be Dup697 (Bioorganic & Medicinal Chemistry Letters, Vol 5, No. 18, p 2123, 1995). Then, as a derivative, SC-58635 (Journal of Medicinal Chemistry, Vol 40, p 1347, 1997) having a pyrrazole structure, MK-966 (WO 95/00501) having a furanone structure and the like are disclosed.

DISCLOSURE OF INVENTION

Based upon the above technical backgrounds, the inventors of the present invention have tried in order to develop novel compounds as a highly selective cyclooxygenase-2 inhibitor. As a result, it is found that diaryl 1,2,4-triazole derivatives of formula 1 containing sulfonamidophenyl or methylsulfonylphenyl group as a specific structure of conventional chemicals satisfies such a purpose.

Therefore, an object of the present invention is to provide diaryl 1,2,4-triazole derivatives of formula 1 and pharmaceutically acceptable salt thereof.

Hereinafter, the present invention will be described more clearly.

The present invention relates to diaryl 1,2,4-triazole derivatives of the following formula 1 and pharmaceutically acceptable salt thereof.

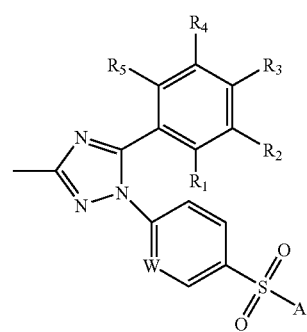

<Formula 1>

Wherein, $R_1$, $R_2$, $R_3$, $R_4$ and $R_5$ are each independently hydrogen; halogen; $C_1$–$C_3$-alkyl not substituted or substituted by halogens; $NO_2$, $NH_2$, OH, OMe, $CO_2H$ or CN and A is $CH_3$ or $NH_2$, and W is CH or N.

The compound of the present invention can also exist as a pharmaceutically acceptable salt form, wherein the pharmaceutically acceptable salt means a nontoxic salt containing organic salt and inorganic salt, being accepted pharmaceutically. The inorganic salt includes aluminum, ammonium, calcium, copper, iron, lithium, magnesium, manganese, potassium, sodium, zinc and the like, and preferably, ammonium, calcium, magnesium, potassium and sodium. The organic salt includes primary-, secondary- or tertiary-amines, naturally substituted amines, cyclic amines, modified salts prepared through basic ion exchange resin and the like. More preferably, the organic salt can be selected from the group consisting of arginine, betain, caffeine, colin, N,N-dibenzylethylenediamine, diethylamine, 2-diethylaminoethanol, 2-dimethylaminoehanol, ethanolamine, ethylenediamine, N-ethylmorpholin, N-ethylpiperidine, N-methylglucamine, glucamine, glucosamine, histidine, hydrapamine, N-(2-hydroxyethyl)piperidine, N-(2-hydroxyethyl)pyrrolidine, isopropylamine, lysine, methylglucamine, morpholin, piperazine, piperidine, polyamine resin, procain, purine, teobromine, triethylamine, trimethylamine, tripropylamine, tromethamine and the like.

Besides, the compound of the present invention can be a salt form of nontoxic acids containing the organic acid and the inorganic acid, being accepted pharmaceutically, in case that it be basic. Preferably, the acid can be selected from the group consisting of acetic acid, adipic acid, aspartic acid, 1,5-naphthalenedisulfonic acid, benzenesulfonic acid, benzoic acid, camposulfonic acid, citric acid, 1,2-ethanedisulfonic acid, ethanesulfonic acid, ethylenediaminetetraacetic acid, fumaric acid, glucoheptonic acid, gluconic acid, glutamic acid, hydriodic acid, hydrobromic acid, hydrochloric acid, icethionic acid, lactic acid, maleic acid, malic acid, manderic acid, methanesulfonic acid, music acid, 2-naphthalenedisulfonic acid, nitric acid, oxalic acid, parnoic acid, pantothenic acid, phosphoric acid, pivalic acid, propionic acid, salicylic acid, stearic acid, succinic acid, sulfuric acid, tartaric acid, p-toluenesulfonic acid, undecanoic acid, 10-undecenoic acid and the like. And more preferably, among succinic acid, hydrobromic acid, hydrochloric acid, maleic acid, methanesulfonic acid, phosphoric acid, sulfuric acid, tartaric acid and the like.

Preferably, the compound of the present invention of formula 1 as a selective inhibitor against cyclooxygenase-2 is that $R_1$, $R_2$, $R_3$, $R_4$, and $R_5$ are each independently hydrogen, halogen, $CH_3$ or $OCH_3$, A is $CH_3$ or $NH_2$, and W is CH or N.

For preferred embodiments of the present invention, the compound of formula 1 will be described more clearly as follows:

4-(3-methyl-5-phenyl-[1,2,4,]triazole-1-yl)-benzenesulfonamide;
4-[5-(4-fluoro-phenyl)-3-mehtyl-[1,2,4]triazole-1-yl]-benzenesulfonamide;
4-[5-(4-chloro-phenyl)-3-mehtyl-[1,2,4]triazole-1-yl]-benzenesulfonamide;
4-[5-(4-bromo-phenyl)-3-mehtyl-[1,2,4]triazole-1-yl]-benzenesulfonamide;
4-(3-methyl-5-p-toly-[1,2,4]trizole-1-yl)-benzenesulfonamide;
4-[5-(4-methoxy-phenyl)-3-methyl-[1,2,4]triazole-1-yl]-benzenesulfonamide;
4-[5-(3-fluoro-phenyl)-3-mehtyl-[1,2,4]triazole-1-yl]-benzenesulfonamide;
4-[5-(3-chloro-phenyl)-3-mehtyl-[1,2,4]triazole-1-yl]-benzenesulfonamide;
4-[5-(3-bromo-phenyl)-3-mehtyl-[1,2,4]triazole-1-yl]-benzenesulfonamide;
4-[5-(3-methoxy-phenyl)-3-methyl-[1,2,4]triazole-1-yl]-benzenesulfonamide;
4-[5-(2-methoxy-phenyl)-3-methyl-[1,2,4]triazole-1-yl]-benzenesulfonamide;
4-[5-(3,4-dimethoxy-phenyl)-3-methyl-[1,2,4]triazole-1-yl]-benzenesulfonamide;
4-[5-(3,5-dimethoxy-phenyl)-3-methyl-[1,2,4]triazole-1-yl]-benzenesulfonamide;
6-(3-methyl-5-phenyl-[1,2,4]triazole-1-yl)-pyridine-3-sulfonic acid amide;
6-[5-(4-fluoro-phenyl)-3-mehtyl-[1,2,4]triazole-1-yl-pyridine-3-sulfonic acid amide;
6-[5-(4-chloro-phenyl)-3-mehtyl-[1,2,4]triazole-1-yl]-pyridine-3-sulfonic acid amide;
6-[5-(4-bromo-phenyl)-3-mehtyl-[1,2,4]triazole-1-yl]-pyridine-3-sulfonic acid amide;
6-(3-methyl-5-p-toly-[1,2,4]triazole-1-yl)-pyridine-3-sulfonic acid amide;
6-[5-(4-methoxy-phenyl)-3-methyl-[1,2,4]triazole-1-yl]-pyridine-3-sulfonic acid amide;
6-[5-(3-fluoro-phenyl)-3-methyl-[1,2,4]triazole-1-yl]-pyridine-3-sulfonic acid amide;
6-[5-(3-chloro-phenyl)-3-methyl-[1,2,4]triazole-1-yl]-pyridine-3-sulfonic acid amide;
6-[5-(3,5-dimethoxy-phenyl)-3-mehtyl-[1,2,4]triazole-1-yl]-pyridine-3-sulfonic acid amide;
1-(4-methanesulfonyl-phenyl)-3-methyl-5-phenyl-1H-[1,2,4]triazole;
5-(4-fluoro-phenyl)-1-(4-methanesulfonyl-phenyl)-3-methyl-1H-[1,2,4]triazole;
5-(4-chloro-phenyl)-1-(4-methanesulfonyl-phenyl)-3-methyl-1H-[1,2,4]triazole;
5-(4-bromo-phenyl)-1-(4-methanesulfonyl-phenyl)-3-methyl-1H-[1,2,4]triazole; and
2-[5-(4-bromo-phenyl)-3-mehtyl-[1,2,4]triazole-1-yl]-5-methanesulfonyl-pyridine.

On the other hand, the compounds of formula 1 according to the present invention can be prepared by performing the procedures as illustrated below.

However, the process for preparing the compounds of the present invention will not be restricted to following descriptions, especially in reaction solvents, bases, amounts of used reactants and the like.

Moreover, the compound of the present invention can be prepared by exploiting and combining various synthetic methods described in the present specification or disclosed in other references of those skilled in this arts with a coordinate and arbitrary mode.

Those skilled in the art will appreciate that the conceptions and specific embodiments disclosed in the foregoing description may be readily utilized as a basis for modifying or designing other embodiments.

The compound of formula 1 according to the present invention can be prepared as illustrated schematically in the following reaction formula 1.

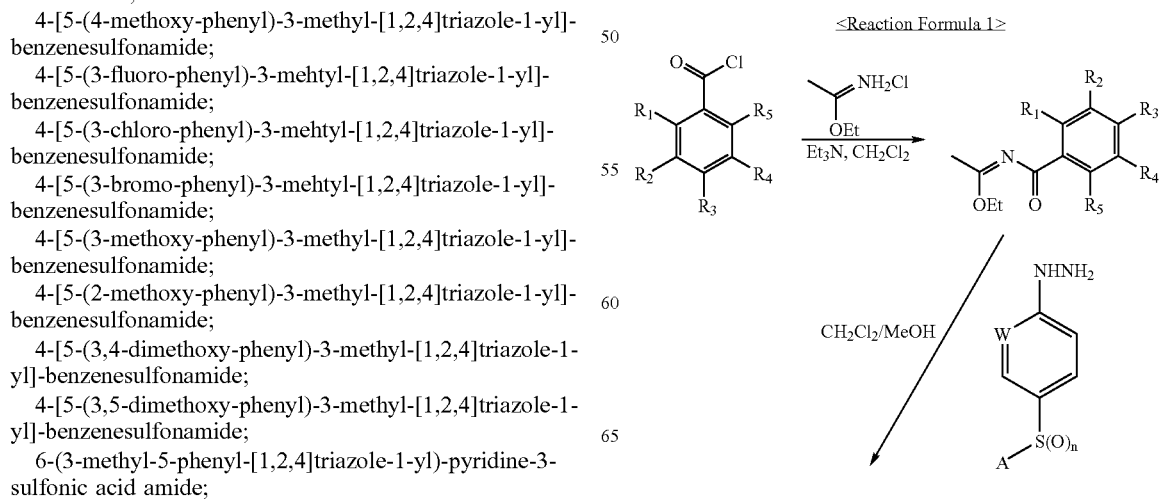

<Reaction Formula 1>

-continued

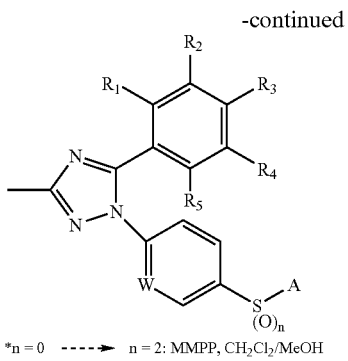

*n = 0 ----▶ n = 2: MMPP, CH₂Cl₂/MeOH

Wherein, $R_1$, $R_2$, $R_3$, $R_4$, $R_5$, W and A are as defined above and n is 0 or 2.

As demonstrated in the above reaction formula 1, the compound of the present invention can be prepared through two steps from benzoyl halide or benzoyl halide derivatives as initial material.

A detailed description on preparing the compound of the present invention by the above method of Reaction formula 1 is as follows.

In the first step, the reaction of ethylacetimidate or its salt and benzoyl halide or benzoyl halide derivatives should be specifically accomplished in the presence of a base. Concretely, the reaction is performed by using dichloromethane at room temperature. The organic base can be selected from the group consisting of triethylamine, trimethylamine, tripropylamine, pyridine, imidazole and the like, while the inorganic base can be selected from the group consisting of sodium acetate, sodium hydroxide, sodium hydride, potassium hydroxide, sodium carbonate, potassium carbonate and the like. More preferably, triethylamine can be used.

In the second step, the reaction forming triazole is carried out by reacting hydrazine compound and the material obtained in the first step in a mixed solvent with dichloromethane and methanol at room temperature. If the hydrazine compound is a salt form, the reaction is carried out in the presence of the base such as triethylamine, trimethylamine, tripropylamine, pyridine, imidazole and the like.

Especially, if the hydrazine compound is n=2, an oxidation reaction process should not be needed, but if the hydrazine compound is n=0, an oxidation reaction process should be carried out at the last step.

The above hydrazine can be selected from the group consisting of 4-methylsulfanylphenyl hydrazine hydrochloride, 4-hydrazinobenzenesulfonamide hydrochloride, 6-hydrazinopyridine-3-sulfonic acid amide and 5-methanesulfonylpyridine-2-yl hydrazine. Among these, 4-methylsulfanylphenyl hydrazine hydrochloride (Tetrahedron Letters, vol 28, No 42, p 4933, 1987) and 6-hydrazinopyridine-3-sulfonic acid amide (U.S. Pat. No. 4,204,870) are synthesized by the disclosed method. 5-methanesulfonylpyridine-2-yl hydrazine (The Journal of Organic Chemistry, vol 56, No 16, p 4974, 1991) is synthesized by applying the disclosed method.

Oxidation reaction for forming sulfonamide or methylsulfone is carried out by using an oxidizer in dichloromethane. The oxidizer can be selected from the group consisting of MMPP (Magnesium monoperoxyphthalate hexahydrate), MCPBA (m-Chloro peroxybenzoic acid), Oxone (Potassium peroxymonosulfate) and the like. More preferably, MMPP can be used.

After completing the reaction, the resulting products can be processed through a common treatment such as chromatography, recrystallization and the like so as to be separated and purified.

The compound of formula 1 according to the present invention has a selective inhibition activity against cyclooxygenase-2 and thus can be employed as an enzymatic inhibitor. The compound of formula 1 as a selective inhibitor against cyclooxygenase-2 can be a substitute for conventional non-steroid anti-inflammatory drugs. Concretely, it improves side effects of anti-inflammatory drugs in conventional non-steroids and is useful in patients suffering from peptic ulcer, gastritis, partial enteritis, ulcerative colitis, diverticulitis, gastrointestinal haemorrhagia, hypoprothrombinemia and the like. Besides, it is expected to be useful for treating inflammatory diseases such as osteoarthritis, rheumatoid arthritis and the like effectively.

The compound of the present invention can be administrated in a single dose or in separated doses, depending upon clinical purposes. The specific dosage for patients will vary, depending upon factors such as a sort of drug compound, body weight, sex, physical condition, diet, administration period, administration method, discharge ratio, drug composition and severity of diseases and the like.

The compound of the present invention can be administered as an oral, a local, a parenteral (subcutaneous, venous and muscular silinge or injection), an inhalational or a rectal drug. In case that these are prepared to a pharmaceutical drug, one or more commonly used vehicles, methods for the preparation and the like can be selected properly from prior arts widely known to those skilled.

In order to attain the desired purpose of clinical administration, the active compound of formula 1 of the present invention can be administered simultaneously with more than one component of other conventional drugs.

However, the pharmaceutical drugs containing the compound of the present invention is not limited to forms described in the above, if it has a purpose for inhibiting cyclooxygenase-2 selectively. All kinds of drugs useful for the enzymatic inhibition can be within the scope of the present invention.

MODES FOR CARRYING OUT THE INVENTION

Practical and presently preferred embodiments of the present invention are illustrated as shown in the following Examples.

However, it will be appreciated that those skilled in the art, on consideration of this disclosure, may make modifications and improvements within the spirit and scope of the present invention.

REFERENCE EXAMPLE 1

Preparation of N-(1-ethoxy-ethylidene)-benzamide

Ethylacetamidate hydrochloride 1.0 g (8.09 mmol) was dissolved in dichloromethane 40 ml at room temperature, added dropwise triethylamine 1.08 ml (16.99 mmol) and stirred for 30 minutes at room temperature. Then, the reacting solution was cooled to 0° C., benzoylchloride 1.03 g (7.35 mmol) was slowly added dropwise in the reacting solution for 10 minutes and stirred for 4 hours at room temperature. After completing the reaction, the reacting solution was washed with water and saturated brine, and then dried with anhydrous magnesium sulfate. Then, the resulting product was filtered under reduced pressure and purified through a flash column chromatography (ethyl acetate:normal hexane=2:8). As a result, N-(1-ethoxy-ethylidene)-benzamide (1.20 g, yield: 86%) was obtained as a liquid phase.

$^1$H-NMR(400 MHz, CDCl$_3$) δ 1.25 (t, 3H, J=7.1 Hz), 1.96 (s, 3H), 4.20 (q, 2H, J=7.1 Hz), 7.32–7.38 (m, 2H), 7.43–7.46 (m, 1H), 7.90–7.95 (m, 2H)

REFERENCE EXAMPLE 2

Preparation of
N-(1-ethoxy-ethylidene)-4-methyl-benzamide

The reaction was carried out through the same method with Reference Example 1, except exploiting p-tolychloride 1.14 g (7.35 mmol) instead of benzoylchloride. As a result, N-(1-ethoxy-ethylidene)-4-methyl-benzamide (1.23 g, yield: 81%) was obtained as a liquid phase.

$^1$H-NMR(400 MHz, CDCl$_3$) δ 1.25 (t, 3H, J=7.1 Hz), 1.96 (s, 3H), 2.40 (s, 3H), 4.20 (q, 2H, J=7.1 Hz), 7.28–7.33 (m, 2H), 7.90–7.95 (m, 2H)

REFERENCE EXAMPLE 3

Preparation of
N-(1-ethoxy-ethylidene)-4-methoxy-benzamide

The reaction was carried out through the same method with Reference Example 1, except employing p-chloroanisole 1.25 g (7.35 mmol) instead of benzoylchloride. As a result, N-(1-ethoxy-ethylidene)-4-methoxy-benzamide (1.28 g, yield: 79%) was obtained as a liquid phase.

$^1$H-NMR(400 MHz, CDCl$_3$) δ 1.25 (t, 3H, J=7.1 Hz), 1.96 (s, 3H), 3.79 (s, 3H), 4.20 (q, 2H, J=7.1 Hz), 7.28–7.33 (m, 2H), 7.90–7.95 (m, 2H)

REFERENCE EXAMPLE 4

Preparation of
N-(1-ethoxy-ethylidene)-4-fluoro-benzamide

The reaction was carried out through the same method with Reference Example 1, except employing 4-fluorobenzoylchloride 1.17 g (7.35 mmol) instead of benzoylchloride. As a result, N-(1-ethoxy-ethylidene)-4-fluoro-benzamide (1.17 g, yield: 76%) was obtained as a liquid phase.

$^1$H-NMR(400 MHz, CDCl$_3$) δ 1.25 (t, 3H, J=7.1 Hz), 1.96 (s, 3H), 4.20 (q, 2H, J=7.1 Hz), 7.28–7.33 (m, 2H), 7.90–7.95 (m, 2H)

REFERENCE EXAMPLE 5

Preparation of
N-(1-ethoxy-ethylidene)-4-chloro-benzamide

The reaction was carried out through the same method with Reference Example 1, except employing 4-chlorobenzoylchloride 1.29 g (7.35 mmol) instead of benzoylchloride. As a result, N-(1-ethoxy-ethylidene)-4-chloro-benzamide (1.43 g, yield: 86%) was obtained as a liquid phase.

$^1$H-NMR(400 MHz, CDCl$_3$) δ 1.25 (t, 3H, J=7.1 Hz), 1.96 (s, 3H), 4.20 (q, 2H, J=7.1 Hz), 7.29 (dd, 2H, J$_1$=4.4 Hz, J$_2$=2.4 Hz), 7.91 (dd, 2H, J$_1$=4.0 Hz, J$_2$=2.4 Hz)

REFERENCE EXAMPLE 6

Preparation of
N-(1-ethoxy-ethylidene)-4-bromo-benzamide

The reaction was carried out through the same method with Reference Example 1, except employing 4-bromobenzoylchloride 1.61 g (7.35 mmol) instead of benzoylchloride. As a result, N-(1-ethoxy-ethylidene)-4-bromo-benzamide (1.62 g, yield: 82%) was obtained as a liquid phase.

$^1$H-NMR(400 MHz, CDCl$_3$) δ 1.25 (t, 3H, J=7.1 Hz), 1.96 (s, 3H), 4.20 (q, 2H, J=7.1 Hz), 7.29 (dd, 2H, J$_1$=4.4 Hz, J$_2$=2.4 Hz), 7.91 (dd, 2H, J$_1$=4.0 Hz, J$_2$=2.4 Hz)

REFERENCE EXAMPLE 7

Preparation of
N-(l-ethoxy-ethylidene)-3-fluoro-benzamide

The reaction was carried out through the same method with Reference Example 1, except employing 3-fluorobenzoylchloride 1.17 g (7.35 mmol) instead of benzoylchloride. As a result, N-(1-ethoxy-ethylidene)-3-fluoro-benzamide (1.28 g, yield: 83%) was obtained as a liquid phase.

$^1$H-NMR(400 MHz, CDCl$_3$) δ 1.25 (t, 3H, J=7.1 Hz), 1.96 (s, 3H), 4.20 (q, 2H, J=7.1 Hz), 7.22–7.27 (m, 1H), 7.38–7.44 (m, 1H), 7.68–7.72 (m, 1H), 7.79–7.83 (m, 1H)

REFERENCE EXAMPLE 8

Preparation of
N-(l-ethoxy-ethylidene)-3-chloro-benzamide

The reaction was carried out through the same method with Reference Example 1, except employing 3-chlorobenzoylchloride 1.29 g (7.35 mmol) instead of benzoylchloride. As a result, N-(1-ethoxy-ethylidene)-3-chloro-benzamide (1.41 g, yield: 85%) was obtained as a liquid phase.

$^1$H-NMR(400 MHz, CDCl$_3$) δ 1.25 (t, 3H, J=7.1 Hz), 1.96 (s, 3H), 4.20 (q, 2H, J=7.1 Hz), 7.15–7.31 (m, 2H), 7.75–7.85 (m, 2H)

REFERENCE EXAMPLE 9

Preparation of
N-(1-ethoxy-ethylidene)-3-bromo-benzamide

The reaction was carried out through the same method with Reference Example 1, except employing 3-bromobenzoylchloride 1.61 g (7.35 mmol) instead of benzoylchloride. As a result, N-(1-ethoxy-ethylidene)-3-bromo-benzamide (1.57 g, yield: 79%) was obtained as a liquid phase.

$^1$H-NMR(400 MHz, CDCl$_3$) δ 1.25 (t, 3H, J=7.1 Hz), 1.96 (s, 3H), 4.20 (q, 2H, J=7.1 Hz), 7.13–7.17 (m, 1H), 7.30–7.32 (m, 1H), 7.74–7.76 (m, 1H), 7.83–7.87 (m, 1H)

REFERENCE EXAMPLE 10

Preparation of
N-(1-ehoxy-ethylidene)-3-methoxy-benzamide

The reaction was carried out through the same method with Reference Example 1, except employing m-chloroanisole 1.25 g (7.35 mmol) instead of benzoylchloride. As a result, N-(1-ehoxy-ethylidene)-3-methoxy-benzamide (1.31 g, yield: 81%) was obtained.

¹H-NMR(400 MHz, CDCl₃) δ 1.25 (t, 3H, J=7.1 Hz), 1.96 (s, 3H), 3.75 (s, 3H), 4.20 (q, 2H, J=7.1 Hz), 6.55–6.60 (m, 1H), 6.99–7.02 (m, 1H), 7.03–7.05 (m, 1H), 7.33–7.36 (m, 1H)

REFERENCE EXAMPLE 11

Preparation of
N-(1-ethoxy-ethylidene)-2-methoxy-benzamide

The reaction was carried out through the same method with Reference Example 1, except employing o-chloroanisole 1.25 g (7.35 mmol) instead of benzoylchloride. As a result, N-(1-ethoxy-ethylidene)-2-methoxy-benzamide (1.22 g, yield: 75%) was obtained.

¹H-NMR(400 MHz, CDCl₃) δ 1.25 (t, 3H, J=7.1 Hz), 1.96 (s, 3H), 3.30 (s, 3H), 4.20 (q, 2H, J=7.1 Hz), 7.00 (d, 1H, J=2.1 Hz), 7.10–7.14 (m, 3H)

REFERENCE EXAMPLE 12

Preparation of
N-(1-ethoxy-ethylidene)-3,5-dimethoxy-benzamide

The reaction was carried out through the same method with Reference Example 1, except employing 3,5-dimethoxy benzoylchloride 1.47 g (7.35 mmol) instead of benzoylchloride. As a result, N-(1-ethoxy-ethylidene)-3,5-dimethoxy-benzamide (1.51 g, yield: 82%) was obtained as a liquid phase.

¹H-NMR(400 MHz, CDCl₃) δ 1.25 (t, 3H, J=7.1 Hz), 1.96 (s, 3H), 3.80 (s, 6H), 4.20 (q, 2H, J=7.1 Hz), 6.63 (t, 1H, J=2.3 Hz), 7.15 (d, 2H, J=2.3 Hz)

REFERENCE EXAMPLE 13

Preparation of
N-(1-ethoxy-ethylidene)-3,4-dimethoxy-benzamide

The reaction was carried out through the same method with Reference Example 1, except employing 3,4-dimethoxy benzoylchloride 1.25 g (7.35 mmol) instead of benzoylchloride. As a result, N-(1-ethoxy-ethylidene)-3,4-dimethoxy-benzamide (1.44 g, yield: 78%) was obtained as a liquid phase.

¹H-NMR(400 MHz, CDCl₃) δ 1.25 (t, 3H, J=7.1 Hz), 1.96 (s, 3H), 3.60 (s, 3H), 3.80 (s, 3H), 4.20 (q, 2H, J=7.1 Hz), 6.91 (d, 1H, J=2.1 Hz), 6.98 (s, 1H), 7.01 (d, 1H, J=2.1 Hz)

EXAMPLE 1

Preparation of 4-(3-methyl-5-phenyl-[1,2,4]triazole-1-yl)-benzenesulfonamide

N-(1-ethoxy-ethylidene)-benzamide 400 mg (2.09 mmol) was dissolved in a mixed solvent of dichloromethane 20 ml and methanol 10 ml and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 4-(3-methyl-5-phenyl-[1,2,4]triazole-1-yl)-benzenesulfonamide (368 mg, yield: 56%) was obtained as a solid phase.

¹H-NMR(400 MHz, DMSO-d₆) δ 2.35 (s, 3H), 7.44–7.49 (m, 5H), 7.52 (s, 2H), 7.56 (dt, 2H, J₁=8.7 Hz, J₂=2.5 Hz), 7.89 (dt, 2H, J₁=8.7 Hz, J₂=2.5 Hz)

Melting point : 192~194° C.

EXAMPLE 2

Preparation of 4-[5-(4-fluoro-phenyl)-3-methyl-[1,2,4]triazole-1-yl]-benzenesulfonamide N-(1-ethoxy-ethylidene)-4-fluoro-benzamide 438 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 4-[5-(4-fluoro-phenyl)-3-methyl-[1,2,4]triazole-1-yl]-benzenesulfonamide (424 mg, yield: 61%) was obtained as a solid phase.

¹H-NMR(400 MHz, DMSO-d₆) δ 2.35 (s, 3H), 7.27–7.31 (m, 2H), 7.47–7.51 (m, 2H), 7.52 (s, 2H), 7.56 (dt, 2H, J₁=8.7 Hz, J₂=2.5 Hz), 7.89 (dt, 2H, J₁=8.7 Hz, J₂=2.5 Hz)

Melting point: 220~221° C.

EXAMPLE 3

Preparation of 4-[5-(4-chloro-phenyl)-3-methyl-[1,2,4]triazole-1-yl]-benzenesulfonamide N-(1-ethoxy-ethylidene)-4-chloro-benzamide 472 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane and then, the collected organic layer was washed with saturated brine. The organic layer was dried with anhydrous magnesium sulfate, filtered and concentrated under reduced pressure, and the resulting product was re-crystallized in acetone and hexane phase. As a result, 4-[5-(4-chloro-phenyl)-3-methyl-[1,2,4]triazole-1-yl]-benzenesulfonamide (423 mg, yield: 58%) was obtained as a solid phase.

¹H-NMR(400 MHz, DMSO-d₆) δ 2.35 (s, 3H), 7.46 (dt, 2H, J₁=8.7 Hz, J₂=2.1 Hz), 7.50–7.54 (m, 4H), 7.58 (dt, 2H, J₁=8.7 Hz, J₂=2.5 Hz), 7.89 (dt, 2H, J₁=8.7 Hz, J₂=2.5 Hz)

Melting point: 247~249° C.

EXAMPLE 4

Preparation of 4-[5-(4-bromo-phenyl)-3-methyl-[1,2,4]triazole-1-yl]-benzenesulfonamide N-(1-ethoxy-ethylidene)-4-bromo-benzamide 565 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 4-[5-(4-bromo-phenyl)-3-methyl-[1,2,4]triazole-1-yl]-benzenesulfonamide (600 mg, yield: 73%) was obtained as a solid phase.

$^1$H-NMR(400 MHz, DMSO-$d_6$) δ 2.35 (s, 3H), 7.39 (dt, 2H, $J_1$=9.0 Hz, $J_2$=2.2 Hz), 7.51 (s, 2H), 7.58 (dt, 2H, $J_1$=9.1 Hz, $J_2$=2.4 Hz), 7.67 (dt, 2H, $J_1$=9.1 Hz, $J_2$=2.4 Hz), 7.91 (dt, 2H, $J_1$=9.2 Hz, $J_2$=2.4 Hz)

Melting point: 240~241° C.

EXAMPLE 5

Preparation of 4-(3-methyl-5-p-toly-[1,2,4]triazole-1-yl)-benzenesulfonamide

N-(1-ethoxy-ethylidene)-4-methyl-benzamide 429 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 4-(3-methyl-5-p-toly-[1,2,4]triazole-1-yl)-benzenesulfonamide (467 mg, yield: 68%) was obtained as a solid phase.

$^1$H-NMR(400 MHz, DMSO-d6) δ 2.30 (s, 3H), 2.35 (s, 3H), 7.18 (d, 2H, J=8.1 Hz), 7.31 (d, 2H, J=8.1 Hz), 7.52 (s, 2H), 7.53 (dd, 2H, $J_1$=6.8 Hz, $J_2$=1.9 Hz), 7.91 (dd, 2H, $J_1$=6.8 Hz, $J_2$=1.9 Hz)

Melting point: 248~249° C.

EXAMPLE 6

Preparation of 4-[5-(4-methoxy-phenyl)-3-mehtyl-[1,2,4]triazole-1-yl]-benzenesulfonamide N-(1-ethoxy-ethylidene) -4-methoxy-benzamide 462 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 4-[5-(4-methoxy-phenyl)-3-mehtyl-[1,2,4]triazole-1-yl]-benzenesulfonamide (381 mg, yield: 53%) was obtained as a solid phase.

$^1$H-NMR(400 MHz, DMSO-$d_6$) δ 2.35 (s, 3H), 3.78 (s, 3H), 6.98 (d, 2H, J=8.9 Hz), 7.37 (d, 2H, J=8.9 Hz), 7.52 (s, 2H), 7.56 (d,2H, J=8.7 Hz), 7.91 (d, 2H, J=8.7 Hz)

Melting: 230~231° C.

EXAMPLE 7

Preparation of 4-[5-(3-fluoro-phenyl)-3-methyl-[1,2,4]triazole-1-yl]-benzenesulfonamide N-(1-ethoxy-ethylidene)-3-fluroro-benzamide 438 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then the collected organic layer was washed with saturated brine. The organic layer was dried with anhydrous magnesium sulfate, filtered and concentrated under reduced pressure, and the resulting product was re-crystallized in acetone and hexane phase. As a result, 4-[5-(3-fluoro-phenyl)-3-methyl-[1,2,4]triazole-1-yl]-benzenesulfonamide (382 mg, yield: 55%) was obtained as a solid phase.

$^1$H-NMR(400 MHz, DMSO-$d_6$) δ 2.35 (s, 3H), 7.22–7.38 (m, 3H), 7.45–7.50 (m, 1H), 7.53 (s, 2H), 7.58 (dt, 2H, $J_1$=8.6 Hz, $J_2$=2.4 Hz), 7.91 (dt, 2H, $J_1$=8.6 Hz, $J_2$=2.4 Hz)

Melting point: 197~199° C.

EXAMPLE 8

Preparation of 4-[5-(3-chloro-phenyl)-3-methyl-[1,2,4]triazole-1-yl]-benzenesulfonamide N-(1-ethoxy-ethylidene) -3-chloro-benzamide 472 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 4-[5-(3-chloro-phenyl)-3-methyl-[1,2,4]triazole-1-yl]-benzenesulfonamide (517 mg, yield: 71%) was obtained as a solid phase.

$^1$H-NMR(400 MHz, DMSO-$d_6$) δ 2.35 (s, 3H), 7.30 (d, 1H, J=6.8 Hz), 7.45 (t, 1H, J=7.7 Hz), 7.51–7.62 (m, 6H), 7.91 (d, 2H, J=8.3 Hz)

Melting point: 146~147° C.

EXAMPLE 9

Preparation of 4-[5-(3-bromo-phenyl)-3-methyl-[1,2,4]triazole-1-yl]-benzenesulfonamide N-(1-ethoxy-ethylidene)-3-bromo-benzamide 565 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the organic layer was washed with saturated brine. The organic layer was dried with anhydrous magnesium sulfate, filtered and concentrated under reduced pressure, and the resulting product was re-crystallized in acetone and hexane phase. As a result, 4-[5-(3-bromo-phenyl)-3-methyl-[1,2,4]triazole-1-yl]-benzenesulfonamide (543 mg, yield: 66%) was obtained as a solid phase.

$^1$H-NMR(400 MHz, DMSO-$d_6$) δ 2.35 (s, 3H), 7.33–7.41 (m, 2H), 7.53 (s, 2H), 7.58 (dt, 2H, $J_1$=9.2 Hz, $J_2$=2.5 Hz), 7.68–7.73 (m, 2H), 7.91 (dt, 2H, $J_1$=8.8 Hz, $J_2$=2.5 Hz)

Melting point : 152~153° C.

EXAMPLE 10

Preparation of 4-[5-(3-methoxy-phenyl)-3-methyl-[1,2,4]triazole-1-yl]-benzenesulfonamide N-(1-ethoxy-ethylidene)-3-methoxy-benzamide 462 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 4-[5-(3-methoxy-phenyl)-3-methyl-[1,2,4]triazole-1-yl]-benzenesulfonamide (503 mg, yield: 70%) was obtained as a solid phase.

$^1$H-NMR(400 MHz, DMSO-$d_6$) δ 2.35 (s, 3H), 3.70 (s, 3H), 6.85–7.07 (m, 3H), 7.31 (t, 1H, J=8.0 Hz), 7.51 (s, 2H), 7.58 (dd, 2H, $J_1$=6.6 Hz, $J_2$=1.9 Hz), 7.91 (dd, 2H, $J_1$=6.6 Hz, $J_2$=1.9 Hz)

Melting point: 211~212° C.

EXAMPLE 11

Preparation of 4-[5-(2-methoxy-phenyl)-3-methyl-[1,2,4]triazole-1-yl]-benzenesulfonamide N-(1-ethoxy-ethylidene)-2-methoxy-benzamide 462 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was purified through a flash column chromatography (ethyl acetate:normal hexane=7:3). As a result, 4-[5-(2-methoxy-phenyl)-3-methyl-[1,2,4]triazole-1-yl]-benzenesulfonamide (86 mg, yield: 12%) was obtained as a liquid phase.

$^1$H-NMR(400 MHz, DMSO-$d_6$) δ 2.35 (s, 3H), 3.25 (s, 3H), 7.04 (d, 1H, J=8.2 Hz), 7.12 (dt, 1H, $J_1$=7.4 Hz, $J_2$=1.0 Hz), 7.38–7.45 (m, 4H), 7.49–7.55 (m, 2H), 7.81 (dt, 2H, $J_1$=8.7 Hz, $J_2$=1.9 Hz)

EXAMPLE 12

Preparation of 4-[5-(3,4-dimethoxy-phenyl)-3-mehtyl-[1,2,4]triazole-1-yl]-benzenesulfonamide N-(1-ethoxy-ethylidene)-3,4-dimethoxy-benzamide 536 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 4-[5-(3,4-dimethoxy-phenyl)-3-mehtyl-[1,2,4]triazole-1-yl]-benzenesulfonamide (575 mg, yield: 72%) was obtained as a solid phase.

$^1$H-NMR(400 MHz, DMSO-$d_6$) δ 2.35 (s, 3H), 3.57 (s, 3H), 3.80 (s, 3H), 7.92–7.03 (m, 3H), 7.51 (s, 1H), 7.58 (dt, 1H, $J_1$=9.1 Hz, $J_2$=2.6 Hz), 7.91 (dt, 2H, $J_1$=9.1 Hz, $J_2$=2.6 Hz)

Melting point: 176~178° C.

EXAMPLE 13

Preparation of 4-[5-(3,5-dimethoxy-phenyl)-3-methyl-[1,2,4]triazole-1-yl]-benzenesulfonamide N-(1-ethoxy-ethylidene)-3,5-dimethoxy-benzamide 536 mg (2.09 mmol) was dissolved in a mixed solvent of dichloromethane 20 ml and methanol 10 ml, and 4-hydrazinobenzenesulfonamide hydrochloride 515 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 4-[5-(3,5-dimethoxy-phenyl)-3-methyl-[1,2,4]triazole-1-yl]-benzenesulfonamide (551 mg, yield: 69%) was obtained as a solid phase.

$^1$H-NMR(400 MHz, DMSO-$d_6$) δ 2.35 (s, 3H), 3.65 (s, 6H), 6.54 (d, 2H, J=2.2 Hz), 6.60 (t, 1H, J=2.3 Hz), 7.51 (s, 1H), 7.58 (dt, 1H, $J_1$=9.1 Hz, $J_2$=2.4 Hz), 7.91 (dt, 2H, $J_1$=9.1 Hz, $J_2$=2.4 Hz)

Melting point: 207~208° C.

EXAMPLE 14

Preparation of 6-(3-methyl-5-phenyl-[1,2,4]triazole-1-yl)-pyridine-3-sulfonic acid amide N-(1-ethoxy-ethylidene)-benzamide 400 mg (2.09 mmol) was dissolved in a mixed solvent of dichloromethane 20 ml and methanol 10 ml, and 6-hydrazinopyridine-3-sulfonic acid amide 433 mg (2.23 mmol) was added to the solution and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 6-(3-methyl-5-phenyl-[1,2,4]triazole-1-yl)-pyridine-3-sulfonic acid amide (336 mg, yield: 51%) was obtained as a solid phase.

$^1$H-NMR(400 MHz, DMSO-d$_6$) δ 2.35 (s, 3H), 7.40–7.51 (m, 5H), 7.73 (s, 2H), 7.98 (d, 1H, J=8.5 Hz), 8.43 (dd, 1H, J$_1$=8.4 Hz, J$_2$=2.4 Hz), 8.68 (dd, 1H, J$_1$=2.5 Hz, J$_2$=0.5 Hz)

Melting point: 203~204° C.

EXAMPLE 15

Preparation of 6-[5-(4-fluoro-phenyl)-3-methyl-[1,2,4]triazole-1-yl]-pyridine-3-sulfonic acid amide N-(1-ethoxy-ethylidene)-4-fluoro-benzamide 438 mg (2.09 mmol) was dissolved in a mixed solvent of dichloromethane 20 ml and methanol 10 ml, and 6-hydrazinopyridine-3-sulfonic acid amide 433 mg (2.23 mmol) was added to the solution and stirred for 8 hours. After completing the reaction, water 20 ml was added to the reacting solution and extracted two times with dichloromethane, and then, the organic layer was washed with saturated brine. The organic layer was dried with anhydrous magnesium sulfate, filtered and concentrated under reduced pressure, and the resulting product was re-crystallized in acetone and hexane phase. As a result, 6-[5-(4-fluoro-phenyl)-3-methyl-[1,2,4]triazole-1-yl]-pyridine-3-sulfonic acid amide (391 mg, yield: 56%) was obtained as a solid phase.

$^1$H-NMR(400 MHz, DMSO-d$_6$) δ 2.35 (s, 3H), 7.25–7.31 (m, 2H), 7.55–7.69 (m, 2H), 7.73 (s, 2H), 7.98 (dd, 1H, J$_1$=8.5 Hz, J$_2$=0.5 Hz), 8.43 (dd, 1H, J$_1$=8.5 Hz, J$_2$=2.4 Hz), 8.68 (dd, 1H, J$_1$=2.4 Hz, J$_2$=0.5 Hz)

Melting point: 221~222° C.

EXAMPLE 16

Preparation of 6-[5-(4-chloro-phenyl)-3-methyl-[1,2,4]triazole-1-yl]-pyridine-3-sulfonic acid amide N-(1-ethoxy-ethylidene) -4-chloro-benzamide 472 mg (2.09 mmol) was dissolved in a mixed solvent of dichloromethane 20 ml and methanol 10 ml, and 6-hydrazinopyridine-3-sulfonic acid amide 433 mg (2.23 mmol) was added to the solution and stirred for 8 hours. After completing the reaction, water 20 ml was added to the reacting solution and extracted two times with dichloromethane, and then, the organic layer was washed with saturated brine. The organic layer was dried with anhydrous magnesium sulfate, filtered and concentrated under reduced pressure, and the resulting product was re-crystallized in acetone and hexane phase. As a result, 6-[5-(4-chloro-phenyl)-3-methyl-[1,2,4]triazole-1-yl]-pyridine-3-sulfonic acid amide (446 mg, yield: 61%) was obtained as a solid phase.

$^1$H-NMR(400 MHz, DMSO-d$_6$) δ 2.35 (s, 3H), 7.45–7.51 (m, 4H), 7.73 (s, 2H), 7.98 (dd, 1H, J$_1$=8.5 Hz, J$_2$=0.5 Hz), 8.43 (dd, 1H, J$_1$=8.5 Hz, J$_2$=2.4 Hz), 8.68 (d, 1H, J=1.6 Hz)

Melting point: 215~217° C.

EXAMPLE 17

Preparation of 6-[5-(4-bromo-phenyl)-3-methyl-[1,2,4]triazole-1-yl]-pyridine-3-sulfonic acid amide N-(1-ethoxy-ethylidene)-4-bromo-benzamide 565 mg (2.09 mmol) was dissolved in a mixed solvent of dichloromethane 20 ml and methanol 10 ml, and 6-hydrazinopyridine-3-sulfonic acid amide 433 mg (2.23 mmol) was added to the solution and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 6-[5-(4-bromo-phenyl)-3-methyl-[1,2,4]triazole-1-yl]-pyridine-3-sulfonic acid amide (437 mg, yield: 53%) was obtained as a solid phase.

$^1$H-NMR (400 MHz, DMSO-d$_6$) δ 2.35 (s, 3H), 7.45–7.48 (m, 2H), 7.63–7.66 (m, 2H), 7.72 (s, 2H), 7.98 (dd, 1H, J$_1$=8.4 Hz, J$_2$=0.6 Hz), 8.41 (dd, 1H, J$_1$=8.6 Hz, J$_2$=2.5 Hz), 8.68 (dd, 1H, J$_1$=2.3 Hz, J$_2$=0.6 Hz)

Melting point: 221~222° C.

EXAMPLE 18

Preparation of 6-(3-methyl-5-p-toly-[1,2,4]triazole-1-yl)-pyridine-3-sulfonic acid amide N-(1-ethoxy-ethylidene)-4-methyl-benzamide 429 mg (2.09 mmol) was dissolved in a mixed solvent of dichloromethane 20 ml and methanol 10 ml, and 6-hydrazinopyridine-3-sulfonic acid amide 433 mg (2.23 mmol) was added to the solution and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 6-(3-methyl-5-p-toly-[1,2,4]triazole-1-yl)-pyridine-3-sulfonic acid amide (372 mg, yield: 54%) was obtained as a solid phase.

$^1$H-NMR(400 MHz, DMSO-d$_6$) δ 2.35 (s, 3H), 2.40 (s, 3H), 7.20 (d, 2H, J=8.0 Hz), 7.35 (d, 2H, J=8.2 Hz), 7.69 (s, 2H), 7.90 (d, 1H, J=8.4 Hz), 8.38 (dd, 1H, J$_1$=8.5 Hz, J$_2$=2.5 Hz), 8.68 (t, 1H, J=0.7 Hz)

Melting point: 198~199° C.

EXAMPLE 19

Preparation of 6-[5-(4-methoxy-phenyl)-3-mehtyl-[1,2,4]triazole-1-yl]-pyridine-3-sulfonic acid amide N-(1-ethoxy-ethylidene)-4-methoxy-benzamide 462 mg (2.09 mmol) was dissolved in a mixed solvent of dichloromethane 20 ml and methanol 10 ml, and 6-hydrazinopyridine-3-sulfonic acid amide 433 mg (2.23 mmol) was added to the solution and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 6-[5-(4-methoxy-phenyl)-3-mehtyl-[1,2,4]triazole-1-yl]-pyridine-3-sulfonic acid amide (397 mg, yield: 55%) was obtained as a solid phase.

$^1$H-NMR(400 MHz, DMSO-d$_6$) δ 2.35 (s, 3H), 3.78 (s, 3H), 6.98 (dt, 2H, J$_1$=9.7 Hz, J$_2$=6.0 Hz), 7.42 (dt, 2H, J$_1$=7.6 Hz, J$_2$=2.9 Hz), 7.73 (s, 2H), 7.98 (dd, 1H, J$_1$=8.7 Hz, J$_2$=0.6 Hz), 8.43 (dd, 1H, J$_1$=8.4 Hz, J$_2$=3.4 Hz), 8.68 (dd, 1H, J=2.4 Hz, J$_2$=0.6 Hz)

Melting point: 191~192° C.

EXAMPLE 20

Preparation of 6-[5-(3-fluoro-phenyl)-3-mehtyl-[1,2,4]triazole-1-yl]-pyridine-3-sulfonic acid amide N-(1-ethoxy-ethylidene)-3-fluoro-benzamide 438 mg (2.09 mmol) was dissolved in a mixed solvent of dichloromethane 20 ml and methanol 10 ml, and 6-hydrazinopyridine-3-sulfonic acid amide 433 mg (2.23 mmol) was added to the solution and stirred for 8 hours. After completing the reaction, water 20 ml was added to the reacting solution and extracted two times with dichloromethane, and then the collected organic layer was washed with saturated brine. The organic layer was dried with anhydrous magnesium sulfate, filtered and concentrated under reduced pressure, and the resulting product was re-crystallized in acetone and hexane phase. As a result, 6-[5-(3-fluoro-phenyl)-3-mehtyl-[1,2,4]triazole-1-yl]-pyridine-3-sulfonic acid amide (370 mg, yield: 53%) was obtained as a solid phase.

$^1$H-NMR(400 MHz, DMSO-$d_6$) δ 2.35 (s, 3H), 7.30–7.38 (m, 3H), 7.43–7.51 (m, 1H), 7.73 (s, 2H), 7.98 (d, 1H, J=8.1 Hz), 8.43 (dd, 1H, $J_1$=8.5 Hz, $J_2$=2.4 Hz), 8.68 (d, 1H, J=1.9 Hz)

Melting point: 195~196° C.

EXAMPLE 21

Preparation of 6-[5-(3-chloro-phenyl)-3-methyl-[1,2,4]triazole-1-yl]-pyridine-3-sulfonic acid amide N-(1-ethoxy-ethylidene)-3-chloro-benzamide 472 mg (2.09 mmol) was dissolved in a mixed solvent of dichloromethane 20 ml and methanol 10 ml, and 6-hydrazinopyridine-3-sulfonic acid amide 433 mg (2.23 mmol) was added to the solution and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 6-[5-(3-chloro-phenyl)-3-methyl-[1,2,4]triazole-1-yl]-pyridine-3-sulfonic acid amide (358 mg, yield: 49%) was obtained as a solid phase.

$^1$H-NMR(400 MHz, DMSO-$d_6$) δ 2.40 (s, 3H), 7.33–7.36 (m, 2H), 7.50–7.58 (m, 1H), 7.61–7.63 (m, 1H), 7.75 (s, 2H), 8.00 (d, 1H, J=8.5 Hz), 8.37 (dd, 1H, $J_1$=8.5 Hz, $J_2$=2.4 Hz), 8.56 (dd, 1H, $J_1$=2.3 Hz, $J_2$=0.5 Hz)

Melting point: 169~168° C.

EXAMPLE 22

Preparation of 6-[5-(3,5-dimethoxy-phenyl)-3-methyl-[1,2,4]triazole-1-yl]-pyridine-3-sulfonic acid amide N-(1-ethoxy-ethylidene)-3,5-dimethoxy-benzamide 536 mg (2.09 mmol) was dissolved in a mixed solvent of dichloromethane 20 ml and methanol 10 ml, and 6-hydrazinopyridine-3-sulfonic acid amide 433 mg (2.23 mmol) was added to the solution and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 6-[5-(3,5-dimethoxy-phenyl)-3-methyl-[1,2,4]triazole-1-yl]-pyridine-3-sulfonic acid amide (496 mg, yield: 62%) was obtained as a solid phase.

$^1$H-NMR (400 MHz, DMSO-d6) δ 2.35 (s, 3H), 3.70 (s, 6H), 6.57–6.62 (m, 2H), 7.73 (s, 2H), 7.98 (dd, 1H, $J_1$=8.5 Hz, $J_2$=1.5 Hz), 8.43 (dd, 1H, $J_1$=8.5 Hz, $J_2$=2.5 Hz), 8.78 (dd, 1H, $J_1$=2.5 Hz, $J_2$=0.5 Hz)

Melting point: 195~196° C.

EXAMPLE 23

Preparation of 3-methyl-1-(4-methylsulfanyl-phenyl)-5-phenyl-1H-[1,2,4]triazole

N-(1-ethoxy-ethylidene)-benzamide 400 mg (2.09 mmol) was dissolved in a mixed solvent of dichloromethane 20 ml and methanol 10 ml, and (4-methylsulfanyl-phenyl)-hydrazine hydrochloride 439 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was purified through a flash column chromatography (ethyl acetate:normal hexane=1:1). As a result, 3-methyl-1-(4-methylsulfanyl-phenyl)-5-phenyl-1H-[1,2,4]triazole (359 mg, yield: 61%) was obtained as a liquid phase.

$^1$H-NMR(400 MHz, DMSO-$d_6$) δ 2.35 (s, 3H), 2.47 (s, 3H), 7.18–22 (m, 4H), 7.23–7.25 (m, 3H), 7.51–7.55 (m, 2H)

EXAMPLE 24

Preparation of 1-(4-methanesulfony-phenyl)-3-methyl-5-phenyl-1H-[1,2,4]triazole 3-methyl-1-(4-methylsulfanyl-phenyl)-5-phenyl-1H-[1,2,4]triazole 281 mg (1.0 mmol) was dissolved in a mixed solvent of dichloromethane 25 ml and methanol 5 ml, and MMPP 800 mg (1.30 mmol) was slowly added to the solution and stirred for 8 hours. After completing the reaction, the reacting solution was filtered, and the mother liquor was washed with sodium hydrogen carbonate and saturated brine, respectively, and then, dried with anhydrous magnesium sulfate, filtered and concentrated under reduced pressure, and the resulting product was purified through a flash column chromatography (ethyl acetate:normal hexane=7:3). As a result, 1-(4-methanesulfony-phenyl)-3-methyl-5-phenyl-1H-[1,2,4]triazole (291 mg, yield: 93%) was obtained as a solid phase.

$^1$H-NMR(400 MHz, DMSO-$d_6$) δ 2.35 (s, 3H), 3.25 (s, 3H), 7.38–7.50 (m, 5H), 7.62 (dd, 2H, $J_1$=6.8 Hz, $J_2$=2.0 Hz), 8.02 (dd, 2H, $J_1$=6.8 Hz, $J_2$=2.0 Hz)

Melting point: 118~119° C.

EXAMPLE 25

Preparation of 5-(4-fluoro-phenyl)-3-mehtyl-1-(4-methylsulfanyl-phenyl)-1H-[1,2,4]triazole N-(1-ethoxy-ethylidene)-4-fluoro benzamide 438 mg (2.09 mmol) was dissolved in a mixed solvent of dichloromethane 20 ml and methanol 10 ml, and (4-methylsulfanyl-phenyl)-hydrazine hydrochloride 439 mg (2.23 mmol)

was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was purified through a flash column chromatography (ethyl acetate:normal hexane=1:1). As a result, 5-(4-fluoro-phenyl)-3-mehtyl-1 2-(4-methylsulfanyl-phenyl)-1H-[1,2,4]triazole (389 mg, yield: 62%) was obtained as a liquid phase.

$^1$H-NMR(400 MHz, DMSO-d$_6$) δ 2.35 (s, 3H), 2.52 (s, 3H), 7.25–7.35 (m, 6H), 7.45–7.51 (m, 2H)

EXAMPLE 26

Preparation of 5-(4-fluoro-phenyl)-1-(4 -methane-sulfonyl-phenyl)-3-methyl-1H-[1,2,4]triazole 5-(4-fluoro-phenyl)-3-methyl-1-(4-methylsulfanyl-phenyl)-1H-[1,2,4]triazole 300 mg (1.0 mmol) was dissolved in a mixed solvent of dichloromethane 25 ml and methanol 5 ml, and MMPP 800 mg (1.30 mmol) was slowly added to the solution and stirred for 8 hours. After completing the reaction, the reacting solution was filtered, and the mother liquor was washed with sodium hydrogen carbonate and saturated brine, respectively, and was dried with anhydrous magnesium sulfate, filtered and concentrated under reduced pressure, and the resulting product was purified through a flash column chromatography (ethyl acetate:normal hexane=7:3). As a result, 5-(4-fluoro-phenyl)-1-(4-methanesulfonyl-phenyl)-3-methyl-1H-[1,2,4]triazole (302 mg, yield: 91%) was obtained as a solid phase.

$^1$H-NMR(400 MHz, DMSO-d$_6$) δ 2.35 (s, 3H), 3.25 (s, 3H), 7.29 (dd, 2H, J$_1$=8.9 Hz, J$_2$=5.4 Hz), 7.50 (dd, 2H, J$_1$=8.9 Hz, J$_2$=5.4 Hz), 7.62 (d, 2H, J=8.8 Hz), 8.02 (d, 2H, J=8.8 Hz)

Melting point: 143~144° C.

EXAMPLE 27

Preparation of 5-(4-chloro-phenyl)-3-methyl-1 -(4-methylsulfanyl-phenyl)-1H-[1,2,4]triazole N-(1-ethoxy-ethylidene)-4-chloro benzamide 472 mg (2.09 mmol) was dissolved in a mixed solvent of dichloromethane 20 ml and methanol 10 ml, and (4-methylsulfanyl-phenyl)-hydrazine hydrochloride 439 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane and then, the collected organic layer was washed with saturated brine. The organic layer was dried with anhydrous magnesium sulfate, filtered and concentrated under reduced pressure, and the resulting product was purified through a flash column chromatography (ethyl acetate:normal hexane=1:1). As a result, 5-(4-chloro-phenyl)-3-methyl-1-(4-methylsulfanyl-phenyl)-1H-[1,2,4]triazole (390 g, yield: 59%) was obtained as a liquid phase.

$^1$H-NMR(400 MHz, DMSO-d$_6$) δ 2.35 (s, 3H), 2.47 (s, 3H), 7.19–7.23 (m, 4H), 7.33 (d, 2H, J=8.6 Hz), 7.42 (d, 2H, J=8.6 Hz)

EXAMPLE 28

Preparation of 5-(4-chloro-phenyl)-1-(4 -methane-sulfonyl-phenyl)-3-methyl-1H-[1,2,4]triazole 5-(4-chloro-phenyl)-3-methyl-1-(4-methylsulfanyl-phenyl)-1H-[1,2,4]triazole 315 mg (1.0 mmol) was dissolved in a mixed solvent of dichloromethane 25 ml and methanol 5 ml, and MMPP 800 mg (1.30 mmol) was slowly added to the solution and stirred for 8 hours. After completing the reaction, the reacting solution was filtered, and the mother liquor was washed with sodium hydrogen carbonate and saturated brine, and then dried with anhydrous magnesium sulfate, filtered and concentrated under reduced pressure, and the resulting product was purified through a flash column chromatography (ethyl acetate:normal hexane=7:3). As a result, 5-(4-chloro-phenyl)-1-(4-methanesulfonyl-phenyl)-3-methyl-1H-[1,2,4]triazole (305 mg, yield: 88%) was obtained as a solid phase.

$^1$H-NMR(400 MHz, DMSO-d$_6$) δ 2.35 (s, 3H), 3.25 (s, 3H), 7.49 (d, 2H, J=8.8 Hz), 7.52 (d, 2H, J=8.8 Hz), 7.65 (d, 2H, J=6.7 Hz), 8.02 (d, 2H, J=6.7 Hz)

Melting point: 184~185° C.

EXAMPLE 29

Preparation of 5-(4-bromo-phenyl)-3-methyl-1 -(4-methylsulfanyl-phenyl)-1H-[1,2,4]triazole N-(1-ethoxy-ethylidene)-4-bromo benzamide 565 mg (2.09 mmol) was dissolved in a mixed solvent of dichloromethane 20 ml and methanol 10 ml, and (4-methylsulfanyl-phenyl)-hydrazine hydrochloride 439 mg (2.23 mmol) was added to the solution. Then, triethylamine 0.35 ml (2.51 mmol) was slowly added dropwise at room temperature for 10 minutes and stirred for 8 hours. After completing the reaction, water 20 ml was added to the reacting solution and extracted two times with dichloromethane, and then the collected organic layer was washed with saturated brine. The organic layer was dried with anhydrous magnesium sulfate, filtered and concentrated under reduced pressure, and the resulting product was purified through a flash column chromatography (ethyl acetate:normal hexane=1:1). As a result, 5-(4-bromo-phenyl)-3-methyl-1-(4-methylsulfanyl-phenyl)-1H-[1,2,4]triazole (497 g, yield: 66%) was obtained as a liquid phase.

$^1$H-NMR(400MHz, DMSO-d$_6$) δ 2.35 (s, 3H), 2.47 (s, 3H), 7.18–7.22 (m, 4H), 7.37 (d, 2H, J=8.7 Hz), 7.49 (d, 2H, J=8.7 Hz)

EXAMPLE 30

Preparation of 5-(4-bromo-phenyl)-1-(4-methane-sulfonyl-phenyl)-3-methyl-1H-[1,2,4]triazole 5-(4-bromo-phenyl)-3-methyl-1-(4-methylsulfanyl-phenyl)-1H-[1,2,4]triazole 360 mg (1.0 mmol) was dissolved in a mixed solvent of dichloromethane 25 ml and methanol 5 ml, and MMPP 800 mg (1.30 mmol) was slowly added to the solution and stirred for 8 hours. After completing the reaction, the reacting solution was filtered, and the mother liquor was washed with sodium hydrogen carbonate and saturated brine, and then dried with anhydrous magnesium sulfate, filtered and concentrated under reduced pressure, and the resulting product was purified through a flash column chromatography (ethyl acetate:normal hexane=7:3). As a result, 5-(4-bromo-phenyl)-1-(4-methanesulfonyl-phenyl)-3-methyl-1H-[1,2,4]triazole (357 mg, yield: 91%) was obtained as a solid phase.

$^1$H-NMR(400 MHz, DMSO-d$_6$) δ 2.35 (s, 3H), 3.25 (s, 3H), 7.41 (d, 2H, J$_1$=6.72 Hz, J$_2$=2.0 Hz), 7.65–7.68 (m, 4H), 8.02 (d, 2H, J=8.6 Hz)

Melting point: 208~209° C.

EXAMPLE 31

Preparation of 2-[5-(4-bromo-phenyl)-3-methyl-[1,2,4]triazole-1-yl]-5-methanesulfonyl-pyridine N-(1-ethoxy-ethylidene)-4-bromo-benzamide 565 mg (2.09 mmol) was dissolved in a mixed solvent of dichloromethane 20 ml and methanol 10 ml, (5-methansulfonyl-pyridine-2-yl)-hydrazine 431 mg(2.23 mmol) was added to the solution and the solution was stirred for 8 hours. After completing the reaction, water 20 ml was added to the reacting solution and extracted two times with dichloromethane, and then, the collected organic layer was washed with saturated brine. The organic layer was dried with anhydrous magnesium sulfate, filtered and concentrated under reduced pressure, and the resulting product was re-crystallized in acetone and hexane phase. As a result, 2-[5-(4-bromo-phenyl)-3-methyl-[1,2,4]triazole-1-yl]-5-methanesulfonyl-pyridine (502 mg, yield: 61%) was obtained as a solid phase.

$^1$H-NMR(400 MHz, DMSO-d$_6$) δ 2.35 (s, 3H), 3.35 (s, 3H), 7.45 (d, 2H, J=8.6 Hz), 7.75 (d, 2H, J=8.6 Hz), 8.02 (dd, 1H, J$_1$=8.7 Hz, J$_2$=0.7 Hz), 8.55 (dd, 1H, J$_1$=8.6 Hz, J$_2$=2.5 Hz), 8.80 (d, 1H, J=1.7 Hz)

Melting point: 211~212° C.

EXPERIMENTAL EXAMPLE

The Selective Inhibition Activity Against cyclooxygenase-2

(1) Experimental procedure

In order to investigate pharmacologically the selective inhibition activity against cyclooxygenase-2 enzyme, the inhibitive effects against cyclooxygenase-1 and cyclooxygenase-2 were measured by two methods as follows.

First, the cyclooxygenase-1 was examined by using U-937 through the following procedure.

The cultured U-937 (humane lymphoma cell, obtained from Korean cell line bank) was centrifuged to collect the pellet. Then, the pellet was diluted with 1×HBSS(Hank's balanced salt solutin) at the concentration of 1×10$^6$ cells/ml, and 1 ml of them was transferred into each well of 12-well plates, and then dissolved with DMSO. 5μl of the diluted sample solution, and 5μl of DMSO vehicle were added therein and mixed, and the mixture was cultured at 37° C. in Co$_2$ incubator for 15 minutes. Arachidonic acid as a substrate was dissolved in ethanol to prepare a stock solution with a concentration of 10 mM, followed by diluting with 1×HBSS to prepare the solution of 1 mM. 10 μl of 1 mM Arachidonic acid solution was added to each of the treated wells, and the mixture was cultured at 37° C. in CO$_2$ incubator for 30 minutes. The cell solution of each well was collected in the centrifuge tube and was centrifuged at 4° C. for 5 minutes at 10,000 rpm. As PGE2 existed in the supernatant separated from collected cell, the concentration of PGE2 was quantitated by using monoclonal kit from Cayman Chemicals, and the concentration of samples and vehicle were compared to estimate the inhibition ratio (%) of each compound against cyclooxygenase-1. Ultimately, the inhibition effect against the cyclooxygenase-1 enzyme was obtained from the result.

Second, the cyclooxygenase-2 was examined by using Raw 264.7 through the following procedure.

After seeding 2×10$^6$ cells of Raw 264.7 cell(obtained from Korean cell line bank) into each of 12-well plates, the wells was treated with aspirin 250 μM and cultured at 37° C. in CO$_2$ incubator for 2 hours. And then, each samples were replaced with new media and cultured for 30 minutes. In addition, the samples was treated with 100 units/ml of interferon Y and 100 ng/ml of lipopolysaccharide(LPS), and cultured for 18 hours. Then, the media was transferred to other tubes and the PGE 2 was quantitated by using EIA kit from Cayman Chemicals.

(2) Experimental results

The experimental results were described in Table 1 as follows.

TABLE 1

Inhibitory effects of cyclooxygenase (COX) (unit: % inhibition)

| | Examples | | | | | |
|---|---|---|---|---|---|---|
| | COX-1 | | | COX-2 | | |
| Concentration | 30 μM | 10 μM | 3 μM | 300 nM | 100 nM | 30 nM |
| Celecoxib (standard substance) | 93.3 | 86.4 | 84.2 | 99.8 | 99.2 | 65.7 |
| 1 | 53.1 | 25.9 | 12.1 | 81.4 | 50.0 | 48.5 |
| 2 | 67.8 | 53.4 | 36.9 | 45.7 | 34.4 | 28.8 |
| 3 | 29.7 | 13.8 | 0.1 | 82.9 | 74.1 | 40.0 |
| 4 | 91.1 | 87.7 | 85.6 | 99.8 | 99.0 | 64.2 |
| 5 | 79.7 | 61.1 | 48.6 | 75.2 | 53.3 | 45.3 |
| 6 | 94.5 | 85.6 | 78.6 | 99.9 | 99.2 | 68.8 |
| 7 | 28.1 | 24.4 | 21.1 | 55.3 | 55.0 | 54.3 |
| 8 | 84.7 | 75.1 | 62.0 | 50.5 | 52.6 | 31.3 |
| 9 | 89.5 | 81.9 | 78.7 | 99.2 | 89.2 | 66.5 |
| 10 | 45.6 | 42.0 | 38.8 | 68.8 | 54.2 | 42.1 |
| 11 | 67.2 | 61.3 | 54.0 | 37.7 | 25.2 | 25.0 |
| 12 | 37.7 | 34.3 | 27.3 | 70.4 | 55.8 | 30.3 |
| 13 | 76.8 | 65.9 | 63.8 | 59.3 | 56.1 | 37.9 |
| 14 | 28.9 | 20.4 | 12.8 | 99.9 | 99.8 | 72.1 |
| 15 | 46.9 | 41.0 | 35.7 | 38.9 | 28.8 | 27.1 |
| 16 | 55.1 | 43.2 | 24.5 | 85.2 | 34.1 | 32.4 |
| 17 | 32.7 | 28.7 | 5.6 | 78.2 | 66.9 | 47.8 |
| 18 | 75.1 | 62.9 | 50.4 | 46.5 | 37.5 | 26.4 |
| 19 | 77.6 | 61.0 | 46.9 | 69.5 | 43.1 | 34.8 |
| 20 | 34.7 | 31.6 | 27.2 | 74.0 | 57.8 | 30.2 |
| 21 | 75.6 | 56.7 | 44.7 | 67.8 | 48.8 | 43.9 |
| 22 | 31.1 | 26.8 | 15.1 | 36.2 | 29.8 | 27.3 |
| 24 | 71.5 | 40.8 | 1.3 | 64.4 | 38.0 | 29.7 |
| 26 | 55.1 | 51.2 | 42.0 | 64.0 | 47.7 | 20.1 |
| 28 | 85.4 | 73.1 | 72.9 | 57.8 | 38.8 | 33.9 |
| 30 | 82.1 | 79.8 | 77.6 | 36.2 | 29.8 | 27.3 |
| 31 | 88.1 | 82.0 | 81.4 | 99.9 | 99.8 | 69.5 |

In vitro experiments were observed to measure the inhibitional ratios against cyclooxygenase-1 and cyclooxygenase-2. Consequently, in case of the compound of Example 4, 6, 9 and 31, the inhibition effect against cyclooxygenase-2 and cyclooxygenase-1 was identified to be similar level in low concentration when comparing with a comparative substance, Celecoxib, which was examined under the same condition. So to speak, the selectivity of the cyclooxygenase-2 is hardly different between the Example and the comparative substance.

Meanwhile, In case of the compound of Example 14, 6-(3-methyl-5-phenyl-[1,2,4]triazole-1-yl)-prydine-3-sulfonic acid amide, the inhibition effect against cyclooxygenase-2 was identified to be more excellent in low concentration than a comparative substance, whereas the inhibition effect against cyclooxygenase-1 was much lower level than a comparative substance. That is to say, the selectivity of cyclooxygenase-2 is confirmed to be better than any other substances, which proves the structural efficacy of diaryl 1,2,4-triazole derivatives in the present invention.

INDUSTRIAL APPLICABILITY

As demonstrated and confirmed above, the novel compound of bipyridinyl derivative is a drug substitute improving side effects of anti-inflammatory drug in conventional non-steroids, and is useful for patients suffering from peptic ulcer, gastritis, partial enteritis, ulcerative colitis, diverticulitis, gastrointestinal haemorrhagia, hypoprothrombinemia and the like. Besides, it is expected to be useful for treating inflammatory diseases such as osteoarthritis, rheumatoid arthritis and the like effectively.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A compound of formula 1 and a pharmaceutically acceptable salt thereof:

[Formula 1]

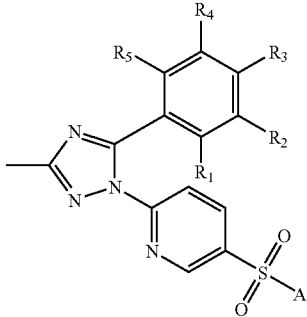

wherein, $R_1$, $R_2$, $R_3$, $R_4$ and R5 are each independently selected from the group consisting of a hydrogen; a halogen; $C_1$–$C_3$-alkyl substituted or not substituted by halogens; $NO_2$, $NH_2$, OH, OMe, $CO_2H$ or CN and A is selected from $CH_3$ or $NH_2$, wherein the compound of formula 1 is selected from the group consisting of:

6-(3-methyl-5-phenyl-[1,2,4]triazole-1-yl)-pyridine-3-sulfonic acid amide;

6-[5-(4-fluoro-phenyl)-3-methyl-[1,2,4]triazole-1-yl]-pyridine-3-sulfonic acid amide;

6-[5-(4-chloro-phenyl)-3-methyl-[1,2,4]triazole-1-yl]-pyridine-3-sulfonic acid amide;

6-[5-(4-bromo-phenyl)-3-methyl-[1,2,4]triazole-1-yl]-pyridine-3-sulfonic acid amide;

6-(3-methyl-5-p-toly-[1,2,4]triazole-1-yl)- pyridine-3-sulfonic acid amide;

6-[5-(4-methoxy-phenyl)-3-methyl-[1,2,4]triazole-1-yl]-pyridine-3-sulfonic acid amide;

6-[5-(3-fluoro-phenyl)-3-methyl-[1,2,4]triazole-1-yl]-pyridine-3-sulfonic acid amide;

6-[5-(3-chloro-phenyl)-3-methyl-[1,2,4]triazole-1-yl]-pyridine-3-sulfonic acid amide;

6-[5-(3,5-dimethoxy-phenyl)-3-methyl-[1,2,4]triazole-1-yl]- pyridine-3-sulfonic acid amide; and 2-[5-(4-bromo-phenyl)-3-methyl-[1,2,4]triazole-1-yl]-5-methanesulfonyl-pyridine.

* * * * *